US007955400B2

(12) United States Patent
Fujinuma et al.

(10) Patent No.: US 7,955,400 B2
(45) Date of Patent: Jun. 7, 2011

(54) TWO-PART HAIR DYE COMPOSITION

(75) Inventors: Hiroyuki Fujinuma, Tokyo (JP);
Takashi Matsuo, Tokyo (JP); Masahiko Ogawa, Tokyo (JP); Takeshi Iizaki, Darmstadt (DE); Hiromi Saimiya, Tokyo (JP); Kazuhiro Okada, Tokyo (JP); Tomohito Koshika, Tokyo (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 12/739,610

(22) PCT Filed: Oct. 24, 2007

(86) PCT No.: PCT/JP2007/001163
§ 371 (c)(1),
(2), (4) Date: Apr. 23, 2010

(87) PCT Pub. No.: WO2009/054029
PCT Pub. Date: Apr. 30, 2009

(65) Prior Publication Data
US 2010/0313905 A1 Dec. 16, 2010

(51) Int. Cl.
*A61Q 5/10* (2006.01)
(52) U.S. Cl. ............. 8/405; 8/431; 8/457; 8/477; 8/526; 8/552; 8/555
(58) Field of Classification Search ............... 8/405, 431, 8/457, 477, 526, 552, 555
See application file for complete search history.

(56) References Cited

U.S. PATENT DOCUMENTS
2004/0213752 A1* 10/2004 Fujinuma et al. ............ 424/70.1
2010/0126522 A1 5/2010 Fujinuma et al.
2010/0126523 A1 5/2010 Fujinuma et al.
2010/0313905 A1 12/2010 Fujinuma et al.
2010/0316583 A1 12/2010 Fujinuma et al.

FOREIGN PATENT DOCUMENTS
| JP | 2004 339216 | 12/2004 |
| JP | 2006 124279 | 5/2006 |
| JP | 2007 314523 | 12/2007 |
| JP | 2007 314524 | 12/2007 |
| WO | 2010/103795 | 9/2010 |
| WO | 2010/103796 | 9/2010 |

OTHER PUBLICATIONS

U.S. Appl. No. 12/739,091, filed Apr. 21, 2010, Fujinuma, et al.
U.S. Appl. No. 12/769,182, filed Apr. 28, 2010, Fujinuma, et al.
U.S. Appl. No. 12/739,835, filed Apr. 26, 2010, Fujinuma, et al.
U.S. Appl. No. 12/739,631, filed Apr. 23, 2010, Miyabe.
U.S. Appl. No. 12/739,471, filed Apr. 23, 2010, Miyabe, et al.
U.S. Appl. No. 12/995,378, filed Nov. 30, 2010, Ogawa et al.
Submission of Publication, JPO, filed on Sep. 15, 2009 p. 1-3 (with English-language Translation).

* cited by examiner

Primary Examiner — Eisa B Elhilo
(74) Attorney, Agent, or Firm — Oblon, Spivak, McClelland, Maier & Neustadt, L.L.P.

(57) ABSTRACT

A two-part hair dye composition, including a first part containing an alkali agent, a second part containing hydrogen peroxide, and a non-aerosol type foamer container for discharging a liquid mixture of the first part and the second part as a foam, wherein the liquid mixture contains the following components (A) to (D): (A) 0.1 to 5% by mass of an alkyl sulfate or polyoxyalkylene alkyl sulfate; (B) 0.1 to 10% by mass of an alkyl polyglucoside; (C) 0.01 to 3% by mass of a dimethyldiallyl ammonium chloride-acrylamide copolymer or a dimethyldiallyl ammonium chloride-acrylamide-acrylic acid copolymer; and (D) 0.01 to 0.8% by mass of a higher alcohol.

6 Claims, 2 Drawing Sheets

TWO-PART HAIR DYE COMPOSITION

FIELD OF THE INVENTION

The present invention relates to a two-part hair dye composition.

BACKGROUND OF THE INVENTION

Conventionally, hair dye compositions in a liquid or cream form have been in widespread use, but it is difficult to evenly apply those compositions to the head hair. In particular, consumers must acquire skills, such as blocking or two mirror technique, to apply the compositions evenly to the root portions of the head hair or to the head hair of an occipital region of the head by themselves, and must carry out operations carefully to apply the compositions evenly.

In view of the foregoing, it has been proposed to simplify hair dyeing operations by discharging an agent as a foam, and for example, a two-part aerosol type and a one-part non-aerosol type have been known. However, the two-part aerosol type composition involves problems in that uneven bleaching and uneven dyeing are likely to occur because the mixing ratio of a first part and a second part does not become constant, a pressure-resistant container and the like made of a metal are oxidized and corroded by hydrogen peroxide, and the internal pressure in the pressure-resistant container is excessively increased owing to the decomposition of hydrogen peroxide. Further, one part non-aerosol type composition involves a problem in that the one part non-aerosol type composition shows no or little bleaching ability enough to cause substantial color tone change in a single application, thereby leaving the composition for a long period of time after the application, or repetitive application of the composition is necessary, resulting in the hair dyeing operations being complicated.

In contrast to the above, products characterized in that a two-part hair dye composition is discharged as a foam from a non-aerosol type foamer container have been proposed (see Patent Documents 1 and 2). In those products, through the discharge of a liquid mixture of a first part and a second part as a foam from a foamer container, the variations of mixing ratio hardly occur compared to the conventional two-part non-aerosol type products, and sufficient bleaching ability or hair dyeing ability may be provided compared to the conventional one part non-aerosol type products.

However, in order to foam a liquid mixture with a non-aerosol type foamer container, the liquid mixture must have a low viscosity, and at the same time, the liquid mixture must be prevented from dripping when being applied to the hair.

Patent Documents 1 and 2 disclose a method of incorporating a higher alcohol to prevent a liquid mixture from dripping. However, in the case of a higher alcohol being used, the problem is that, viscosity of the liquid mixture increases when the liquid temperature is low, for example, in winter season, thereby foaming the liquid mixture with a foamer container being difficult.

[Patent Document 1] JP-A-2004-339216
[Patent Document 2] JP-A-2006-124279

SUMMARY OF THE INVENTION

The present invention provides a two-part hair dye composition, including a first part containing an alkali agent, a second part containing hydrogen peroxide, and a non-aerosol type foamer container for discharging a liquid mixture of the first part and the second part as a foam, in which the liquid mixture includes the following components (A) to (D):

(A) 0.1 to 5 mass % of an alkyl sulfate or a polyoxyalkylene alkyl sulfate;
(B) 0.1 to 10 mass % of an alkyl polyglucoside;
(C) 0.01 to 3 mass % of a dimethyldiallyl ammonium chloride-acrylamide copolymer or a dimethyldiallyl ammonium chloride-acrylamide-acrylic acid copolymer; and
(D) 0.01 to 0.8 mass % of a higher alcohol.

Further, the present invention provides a head hair dyeing method, including: discharging the liquid mixture of the two-part hair dye composition described above as a foam from a non-aerosol type foamer container; applying the foam to a head hair, and then re-foaming on the head hair.

Figure 1:
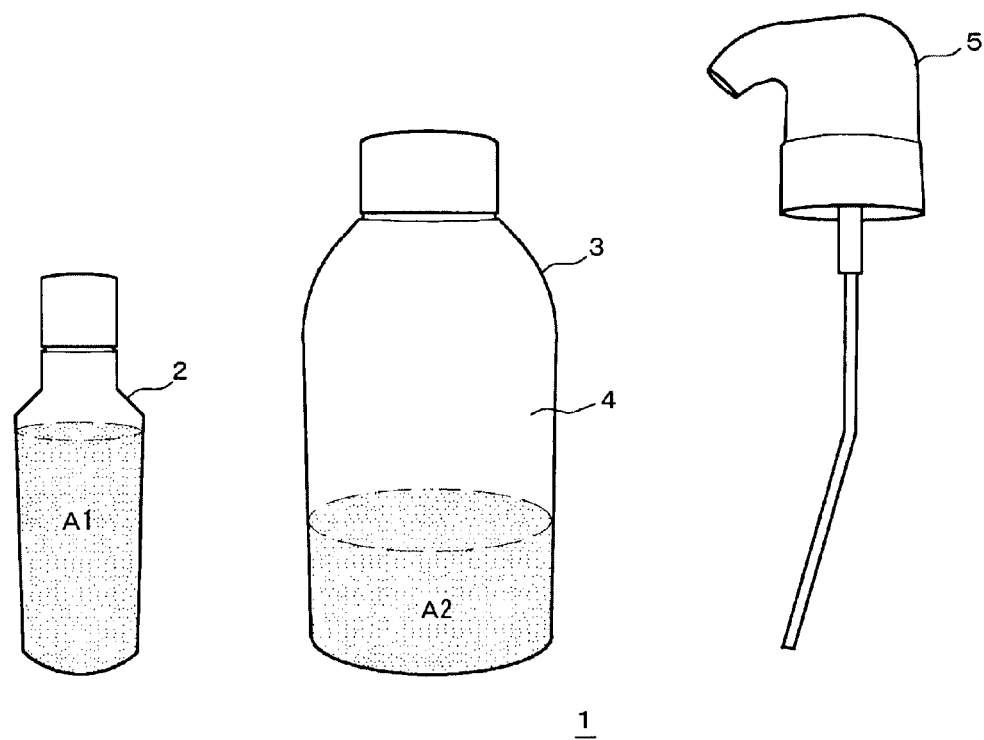
FIG. 1 is a drawing illustrating a two-part hair dye composition before mixing used in Examples and Comparative Examples.

| Description of Symbols | |
| --- | --- |
| 1 | respective components of two-part hair dye composition |
| 2 | first container |
| 3 | second container |
| 4 | container body for squeeze container |
| 5 | squeeze foamer |
| 6 | squeeze container |
| A1 | first part |
| A2 | second part |
| A3 | liquid mixture |

DETAILED DESCRIPTION OF THE INVENTION

The present invention relates to a two-part hair dye composition as a foam, which exhibits satisfactory foaming property even at low temperature, and which causes no liquid dripping during a period from the application of a liquid mixture to the hair to the rinsing away thereof.

The inventors of the present invention have found that the above-mentioned object can be achieved by incorporating a specific anionic surfactant, a specific nonionic surfactant, a specific polymer, and a higher alcohol at a given proportion into a liquid mixture of a first part and a second part in the two-part non-aerosol type hair dye composition.

According to the present invention, the liquid mixture of the two-part hair dye composition is discharged as a foam, and can be applied evenly and simply to the head hair. Further, the foam of the discharged liquid mixture is in a fine state even when the liquid temperature is low in, for example, the winter season, exhibits a good affinity to the head hair, and causes no liquid dripping after the application to the head hair. In addition, the foam does not cause irritation to the scalp and spattering of the composition, and has sufficient bleaching ability or dyeing ability. Therefore, the hair dye composition of the present invention can provide a uniform and more even bleaching finish or hair dyeing finish in a simple and comfort manner.

Further, the liquid mixture discharged as a foam by gas-liquid mixing using a non-aerosol type foamer container easily reaches the roots of the head hair, and the liquid mixture spreads throughout the head hair in an appropriate thin layer without liquid accumulation or the like at the site. Thus, unlike a case of using conventional compositions such as a liquid or cream form, the root portions do not become extremely bright, and uneven bleaching and uneven dyeing due to the uneven adhesion amount of the liquid mixture do not occur. Accordingly, through application of the two-part hair dye composition of the present invention to the head hair in the vicinity of newly growing areas such as the parting and face line, any difference in color between newly growing areas and already dyed areas may also be avoided to provide a natural finish. Further, because the liquid mixture may be applied to the head hair in an appropriate amount, damages to the head hair may be reduced.

DEFINITION

The head hair as used herein refers to hair that grows on the head, and is a concept that excludes hair such as a hairpiece and a tress, which are separated from the head. Further, any head hair derived from a doll and all animals may be used. However, human head hair is preferred.

The two-part hair dye composition as used herein is a concept that includes both of a hair dye composition containing a dye and a bleach composition containing no dye. The head hair dyeing method is a concept that includes a head hair bleaching method.

[Alkali Agent]

For an alkali agent contained in the first part, ammonia, an alkanolamine such as ethanolamine, sodium hydroxide, and potassium hydroxide may be used, for example. Further, optionally, an ammonium salt such as ammonium hydrogen carbonate and ammonium chloride, a carbonate such as potassium carbonate and sodium hydrogen carbonate, and the like may be added as a buffer.

The pH of the liquid mixture of the first part and the second part in the two-part hair dye composition of the present invention is preferably 8 to 11, and more preferably 9 to 11, and the use amount of the alkali agent is appropriately adjusted so that the pH of the liquid mixture falls within the above-mentioned range.

[Hydrogen Peroxide]

The content of hydrogen peroxide in the second part is preferably 1 to 9% by mass, and more preferably 3 to 6% by mass, and the content of hydrogen peroxide in the liquid mixture of the first part and the second part is preferably 1 to 6% by mass, and more preferably 2 to 5% by mass. Further, the pH of the second part is adjusted to preferably 2 to 6, and more preferably 2.5 to 4 in order to prevent the decomposition of the hydrogen peroxide.

(A) and (B): Surfactant

In order that a foam be easily formed by mixing air and the hair dye composition with means for discharging a foam in a foamer container, and the foam be stabilized, a surfactant is incorporated into any one of or both of the first part and the second part. In the present invention, for the surfactant, an alkyl sulfate or a polyoxyalkylene alkyl sulfate as a component (A) and an alkyl polyglucoside as a component (B) are used in combination in order to provide satisfactory foaming property which allows easy application to the head hair even when the liquid temperature is low or is close to normal temperature.

The alkyl sulfate or the polyoxyalkylene alkyl sulfate as the component (A) preferably includes an alkyl group having 10 to 24 carbon atoms, and more preferably 12 to 18 carbon atoms, and further, the alkyl group is preferably linear. In addition, preferred is a polyoxyalkylene alkyl sulfate, and more preferred is a polyoxyethylene alkyl sulfate. Of those, polyoxyethylene alkyl sulfate including an oxyethylene group with an average addition mole number of 1 to 10, and more preferably 2 to 5 is preferred.

The component (A) may be used in a combination of two or more kinds thereof, and the content thereof in the liquid mixture of the first part and the second part is 0.1 to 5% by mass, preferably 0.1 to 1% by mass, and more preferably 0.2 to 0.6% by mass.

The alkyl polyglucoside as the component (B) preferably includes an alkyl group having 8 to 18 carbon atoms, more preferably 8 to 14 carbon atoms, and even more preferably 9 to 11 carbon atoms, and further, the alkyl group is preferably linear. The average polymerization degree of glucoside is preferably 1 to 5, and more preferably 1 to 2.

The component (B) may be used in a combination of two or more kinds thereof, and the content thereof in the liquid mixture of the first part and the second part is 0.1 to 10% by mass, preferably 1 to 5% by mass, and more preferably 2 to 4% by mass.

In order to improve a foam quality at low liquid temperature, the mass ratio of the component (A) to the component (B) (content of component (A)/content of component (B)) in the liquid mixture is preferably 0.05 to 0.8, more preferably 0.07 to 0.6, even more preferably 0.08 to 0.5, and even more preferably 0.1 to 0.3.

When the two-part hair dye composition of the present invention is a hair dye, the first part contains an oxidation dye or a direct dye. For a surfactant to be incorporated into the first part in order to dissolve those dyes, it is preferred to mainly use the alkyl polyglucoside as the component (B) which is a nonionic surfactant in view of the high ionic strength of the first part due to ammonia and a carbonate which are contained in the first part.

Meanwhile, the alkyl sulfate or the polyoxyalkylene alkyl sulfate as the component (A) which is an anionic surfactant is preferably incorporated into the second part in view of the high ionic strength of the first part.

(C) Dimethyldiallyl ammonium chloride-acrylamide copolymer or dimethyldiallyl ammonium chloride-acrylamide-acrylic acid copolymer In a component (C), a dimethyldiallyl ammonium chloride-acrylamide copolymer is Polyquaternium-7 (INCI name), and as commercially available products, there are given such as Merquat 550 (Nalco Company), for example. Further, a dimethyldiallyl ammonium chloride-acrylamide-acrylic acid copolymer is Polyquaternium-39 (INCI name), and as commercially available products, there are given such as Merquat Plus 3330 and Merquat Plus 3331 (which are manufactured by Nalco Company), for example.

The component (C) may be used in a combination of two or more kinds thereof, and is preferably not incorporated into the second part containing an anionic surfactant, but incorporated into the first part in terms of storage stability.

The content of the component (C) in the liquid mixture of the first part and the second part is 0.01 to 3% by mass, preferably 0.1 to 1% by mass, and more preferably 0.2 to 0.5% by mass in order to provide satisfactory foaming property which allows easy application to the head hair even when the liquid temperature is low or is close to normal temperature, and to provide an effect of preventing liquid dripping during a period from the application of the liquid mixture to the hair to the rinsing away thereof.

Further, in order to improve a foam quality at low liquid temperature and prevent liquid dripping, the mass ratio of the component (A) to the component (C) (content of component (A)/content of component (C)) in the liquid mixture is preferably 0.1 to 10, more preferably 0.3 to 7, even more preferably 0.5 to 5, and even more preferably 1 to 3.

(D): Higher Alcohol

A higher alcohol as the component (D) is used in order to improve foam-holding property and to enhance an effect of suppressing liquid dripping during being left to stand after the application of the two-part hair dye composition of the present invention to the head hair. The higher alcohol preferably includes an alkyl group or an alkenyl group having 10 to 30 carbon atoms, more preferably 12 to 24 carbon atoms, and even more preferably 14 to 22 carbon atoms. Of those, a higher alcohol having an alkyl group, and more preferably a linear alkyl group is preferred. Examples of the higher alcohol as the component (D) include myristyl alcohol, cetyl alcohol, stearyl alcohol, behenyl alcohol, isostearyl alcohol, and oleyl alcohol. Those may be used in a combination of two or more kinds thereof.

The component (D) may also be used in a combination of two or more kinds thereof, and may be incorporated into any one of or both of the first part and the second part. The content of the component (D) in the liquid mixture of the first part and the second part is preferably 0.01 to 0.8% by mass, more preferably 0.1 to 0.7% by mass, and even more preferably 0.2 to 0.6% by mass from the viewpoints that the foamability is not inhibited at low liquid temperature, and an effect of suppressing liquid dripping during being left to stand is enhanced.

(E): Dimethyldiallyl ammonium chloride-acrylic acid copolymer

In order to control antifoaming property after the application to the hair, maintain appropriate foam duration, and facilitate the confirmation of an applied portion, as a component (E), a dimethyldiallyl ammonium chloride-acrylic acid copolymer (INCI name: Polyquaternium-22), together with the component (C), may be used in combination in the two-part hair dye composition of the present invention. For example, commercially available products such as Merquat 280 and Merquat 295 (which are manufactured by Nalco Company) may be used as the component (E).

Similar to the component (C), the component (E) is also preferably not incorporated into the second part containing an anionic surfactant, but incorporated into the first part in terms of storage stability. The content of the component (E) in the liquid mixture of the first part and the second part is preferably 0.01 to 0.5% by mass, and more preferably 0.1 to 0.2% by mass in order to provide the above-mentioned effect without inhibiting foaming property at low liquid temperature.

(F): Nonvolatile Hydrophilic Solvent

In addition, it is preferred that a nonvolatile hydrophilic solvent be contained in the first part or the second part. This may reduce the irritation to the scalp due to enrichment of an irritating component such as hydrogen peroxide through water evaporation from the two-part hair dye composition of the present invention during being left to stand after the application of the hair dye composition to the head hair. The nonvolatile hydrophilic solvent that does not have any antifoaming action, such as polyols and lower (1 to 4 carbon atoms) alkyl ethers thereof, is preferable. Preferred are polyols having 2 to 6 carbon atoms, and examples thereof include glycerin, diglycerin, propylene glycol, dipropylene glycol, 1,3-butanediol, ethylene glycol, diethylene glycol, isoprene glycol, and sorbitol. Examples of the lower alkyl ethers of polyols include mono-lower alkyl ethers and poly-lower alkyl ethers (for example, di-lower alkyl ethers) of the above-mentioned polyols. Of those, preferred are monomethyl ethers or monoethyl ethers of polyols, and specific examples thereof include ethylene glycol monomethyl ether, ethylene glycol monoethyl ether, diethylene glycol monomethyl ether, and diethylene glycol monoethyl ether. Two or more kinds of those ethers may be used in combination.

The content of the nonvolatile hydrophilic solvent in the liquid mixture of the first part and the second part is preferably 0.01 to 4% by mass, more preferably 0.1 to 3% by mass, and even more preferably 0.2 to 2% by mass in terms of providing an effect of reducing the irritation to the scalp and a satisfactory foam quality even at low liquid temperature.

[Dye]

The two-part type hair dye composition of the present invention may be used for bleaching the head hair when a dye is not incorporated in the liquid mixture of the first part and the second part, and the composition may be used for hair dyeing by incorporating an oxidation dye or a direct dye into the liquid mixture. When the composition is used for hair dyeing, the first part contains an oxidation dye or a direct dye. Examples of the oxidation dye include: dye precursors such as p-phenylenediamine, toluene-2,5-diamine, o-chloro-p-phenylenediamine, N-phenyl-p-phenylenediamine, N,N-bis(hydroxyethyl)-p-phenylenediamine, 3-methyl-4-aminophenol, 2-hydroxyethyl-p-phenylenediamine, p-aminophenol, p-methylaminophenol, 4-amino-m-cresol, o-aminophenol, 1-hydroxyethyl-4,5-diaminopyrazole, or salts thereof; and couplers such as resorcin, 2-methylresorcin, 1-naphthol, 1,5-dihydroxynaphthalene, 5-amino-o-cresol, m-phenylenediamine, m-aminophenol, 2,4-diaminophenoxyethanol, 2,6-diaminopyridine, 2-methyl-5-hydroxyethylaminophenol, 2-amino-3-hydroxypyridine, or salts thereof.

Examples of the direct dye include a basic dye, a nitro dye, a dispersion dye, and a cationic dye. Further, specific examples thereof include 2-nitro-p-phenylenediamine, 2-amino-6-chloro-4-nitrophenol, 3-nitro-p-hydroxyethylaminophenol, 4-nitro-o-phenylenediamine, 4-amino-3-nitrophenol, 4-hydroxypropylamino-3-nitrophenol, HC Blue 2, HC Orange 1, HC Red 1, HC Yellow 2, HC Yellow 4, HC Yellow 5, HC Red 3, N,N-bis(2-hydroxyethyl)-2-nitro-p-phenylenediamine, Disperse Violet 1, Disperse Blue 1, Disperse Black 9, Basic Blue 99, Basic Brown 16, Basic Brown 17, Basic Red 76, Basic Yellow 76, Basic Orange 31, and Basic Red 51.

[Silicones]

In the two-part type hair dye composition of the present invention, the content of silicone in the liquid mixture of the first part and the second part is preferably 0.5% by mass or less, and more preferably free of silicones in view of enabling a discharged foam to be maintained for a long period of time. However, silicones may be further incorporated within a predetermined range for the foam to fit comfortably to the head hair, and to impart a high conditioning effect to the head hair. Examples of the silicones include dimethylpolysiloxane, methylphenylpolysiloxane, a polyether-modified silicone, an amino-modified silicone, and an oxazoline-modified silicone elastomer, and emulsions obtained by dispersing those silicones in water using a surfactant. Of those, preferred are a polyether-modified silicone, an amino-modified silicone, and an emulsion thereof, because those silicones may be stably dispersed in water without the use of a thickener.

When silicone is used for the above-mentioned purposes, the content of silicones in the liquid mixture of the first part and the second part is preferably 0.01 to 0.5% by mass, more preferably 0.02 to 0.4% by mass, and even more preferably 0.05 to 0.3% by mass.

[Other Components]

In addition to the above, the first part and the second part may contain, depending on its purposes, a fragrance, an ultraviolet absorber, a sequestering agent such as EDTA, a microbicide, a preservative such as methyl p-hydroxybenzoate, a stabilizer such as phenacetin, etidronic acid, and oxyquinoline sulfate, an organic solvent such as ethanol, benzyl alcohol, and benzyloxyethanol, a water-soluble polymeric compound such as polyquaternium-6, polyquaternium-39, and hydroxyethylcellulose, and a humectant, for example. Further, it is preferred that the liquid mixture of the first part and the second part mainly contain water as a medium.

It should be noted that a persulfate such as ammoniumpersulfate may be incorporated as a third part into the liquid mixture in order to further enhance a bleaching effect.

[Viscosity]

The viscosity (25° C.) of the first part is preferably 1 to 50 mPa·s, more preferably 3 to 40 mPa·s, and even more preferably 5 to 30 mPa·s. The viscosity (25° C.) of the second part is preferably 1 to 300 mPa·s, more preferably 3 to 200 mPa·s, and even more preferably 5 to 100 mPa·s. The viscosity (25° C.) of the liquid mixture of the first part and the second part is 1 to 100 mPa·s, preferably 3 to 50 mPa·s, and even more preferably 5 to 30 mPa·s. It should be noted that the value of the viscosity is a value obtained after rotation of a rotor for 1 minute using a No. 1 rotor in a Brookfield rotational viscometer (Model TV-10) manufactured by Tokimec Inc. When a measurement target has a viscosity of 100 mPa·s or less, 100 to 200 mPa·s, and 200 to 500 mPa·s, measurement is performed at a rotation speed of 60 rpm, 30 rpm, and 12 rpm, respectively. The adjustment of the viscosity of the liquid mixture to the above-mentioned range allows homogeneously mixing the liquid mixture without foaming the liquid mixture, and further, may provide uniform foam which is easily applied to the head hair, exhibits a good affinity to the head hair, and hardly causes liquid dripping after the application to the head hair.

The adjustment of the viscosity to the above-mentioned range allows a quality of foam that is easily applied and exhibits good affinity to the head hair to be provided, allows the dripping after the application of the foam to the head hair to be suppressed, and enables the foam to be easily discharged in discharging the foam with a non-aerosol type foamer. In order to adjust the viscosity to the above-mentioned range, it is recommended that a water-soluble solvent such as ethanol be added, or the content and kind of a surfactant, polyols, a higher alcohol, and the like be appropriately adjusted.

[Gas-Liquid Mixing Ratio]

The gas-liquid mixing ratio of air to the liquid mixture in the foam discharged with a foamer container is preferably 10 to 50 mL/g, more preferably 15 to 40 mL/g, and even preferably 20 to 30 mL/g in terms of achieving good affinity and easiness of application of the agent to the hair. It should be noted that the gas-liquid mixing ratio used in this embodiment is a value measured as described below.

The gas-liquid mixing ratio is determined by measuring the mass and the volume of the foam discharged at 25° C. 100 g of a liquid mixture are charged into a foamer container, 20 g of foam are discharged into a 1000-mL measuring cylinder, and the volume of the foam is measured 1 minute after the start of discharge. The gas-liquid mixing ratio (mL/g) can be obtained by dividing the volume (mL) of the discharged foam by the mass of 20 g.

[Foamer Container]

In the present invention, the foamer container is a non-aerosol type container, and is used for mixing a first part and a second part or a liquid mixture thereof with air without using a propellant and discharging the mixture as a foam. The use of the foamer container also provides an effect of preventing the discharged agent from spattering. In particular, in a comparison with an aerosol type container, the non-aerosol type container may be produced at a low production cost, is easily adjusted for the discharge speed, may be recycled by performing a given treatment, and may be handled more safely in a product distribution because the container does not need a high pressure gas propellant.

For the foamer container, any container may also be used as long as being a non-aerosol type container, and having means for discharging foam, such as a known pump foamer container and squeeze foamer container having foam discharging means.

The pump foamer container or the squeeze foamer container has a foam producing portion such as a net, and preferably has a thin net from the viewpoint that, when clogging occurs owing to drying and solidification of the liquid mixture of the first part and the second part, the clogging may be eliminated by instantaneously dissolving the solidified product by a foam flow at the time of the next discharge. In this case, the mesh of the net is preferably 50 to 280 mesh, more preferably 90 to 250 mesh, and even more preferably 130 to 220 mesh. Creamy foam may be produced by using a net having a mesh in the above-mentioned range. Further, a material for such mesh is preferably nylon, polyethylene, polypropylene, polyester, Teflon (registered trademark), a carbon fiber, and stainless, more preferably nylon, polyethylene, polypropylene, and polyester, and even more preferably nylon, for example.

The foamer container to be used in the two-part hair dye composition of the present invention is provided with such net by at least one net, and preferably multiple nets. From the viewpoints of economic efficiency, foam stability, and the like, two nets are more preferred. In this case, it is preferred that the openings of the mesh through which a liquid firstly passes be more rough than or equal to that of the mesh through which the liquid secondly passes.

The Portion (for example, inner wall of container and inner wall of means for discharging foam), which comes into contact with contents in the foamer container, is preferably composed of a material that is not corroded with an alkali and hydrogen peroxide, and is able to pass oxygen resulting from the decomposition of hydrogen peroxide.

With regard to the product form of the two-part hair dye composition of the present invention including the first part, the second part, and the foamer container, the first part and the second part are each charged into a container separated from the foamer container, and both parts may be transferred into the foamer container and mixed with each other before use. Alternatively, one part is charged into the foamer container, the other part is charged into a separate container, and the other part may be transferred into the foamer container before use. In this case, in order to prevent the pressure in the container from being elevated by oxygen resulting from the decomposition of hydrogen peroxide, the second part is charged into preferably a foamer container made of a gas permeable container, and more preferably a foamer container made of an oxygen permeable material (such as polypropylene and polyethylene). Meanwhile, in order to prevent an oxidation dye from being oxidized, a container that hardly passes oxygen is preferable to be used for the first part.

[Head Hair Dyeing Method]

In order to dye the head hair with the two-part hair dye composition of the present invention, it is preferred to discharge the liquid mixture of the first part and the second part as a foam from a non-aerosol type foamer container, to apply the foam to the head hair, then to re-foam the liquid mixture applied foam on the head hair, and to wash the foam away after a lapse of about 3 to 60 minutes, and preferably about 5 to 45 minutes from the application.

In the two-part hair dye composition, the first part and the second part are mixed with each other immediately before use to perform a hair dyeing treatment. In the present invention, the first part and the second part may be mixed in accordance with any one of the following:

1) mixing is performed before being charged into the body of the foamer container;

2) mixing is performed in the body of the foamer container;

3) the first part and the second part are mixed with each other by joining in a gas-liquid mixing chamber in the foamer;

4) the first part and the second part are separately foamed once, and then both foamed agents are merged to be mixed with each other before being discharged from the foamer;

5) the foam of the first part and the foam of the second part, which have been separately discharged, are mixed with each other before being applied to the head hair; and 6) the foam of the first part and the foam of the second part, which have been separately discharged, are mixed with each other on the head hair.

Of those, from the viewpoints of allowing simplifying the structure of the foamer container, freely designing the compositions of the first part and the second part, and mixing in a reliable and uniform manner, it is preferred that 1) mixing is performed before being charged into the body of the foamer container, or 2) mixing is performed in the body of the foamer container.

It is preferred to comb the head hair in advance before the discharged foam is applied. This prevents the hair from being highly entangled during the re-foaming treatment, and hence, there is no fear of spattering the hair dye composition. Further, after the head hair has been combed, it is not necessary to perform a blocking operation which has been commonly used in the application of the hair dye composition, and further, it is preferred that the blocking operation be not performed. This facilitates an operation of applying the hair dye composition to the head hair and an operation of re-foaming as described later.

To the head hair to which the hair dye composition is applied, it is preferred to apply no hair dressing immediately before a hair dyeing treatment from the viewpoints of achieving even hair dyeing, preventing liquid dripping, and providing a sufficient hair dyeing effect. Further, the head hair is preferably being dried from the viewpoints of causing no dilution in the liquid mixture, achieving even hair dyeing, preventing liquid dripping, and providing a sufficient hair dyeing effect. In the case of rinsing the hair immediately before a hair dyeing treatment, the head hair is preferably dried before the hair dyeing treatment. The phrase "head hair is dried" refers that a liquid mainly containing water deposited by rinsing the hair is removed at least to such an extent that the liquid does not drip in a natural state. Specifically, it is preferred to dry the hair with a towel or a dryer.

The liquid mixture of the first part and the second part discharged as a foam is applied to the head hair after having been taken in hand or a brush, or directly. Here, in the case of performing the application by hand, it is preferred to protect the hand with a glove. According to the dyeing method of the present invention, because it is not necessary to perform a blocking operation which has been generally used in the application of the hair dye composition, the foam may be applied in a short period of time. Thus, the head hair site to which foam is applied first may be any portion, and it is not necessary to apply the foam first to the border of the back hair, unlike a conventional two-part hair dye composition in a liquid or cream form. It is preferable to apply the foam first to a portion of concern, and it is preferable to apply the foam first to the hairline or parting portion of the head hair.

It is preferred to discharge foam in an amount close to the size of a lemon because the amount is suitable for taking the foam in one hand and is easily applied by hand to the head hair. In this case, an operation of discharging foam is performed by one hand, and the foam is taken in the other hand. Then, operations of applying the foam taken in hand once to the head hair, and then discharging foam in hand again to apply the foam to the head hair are repeated. This series of operations may be performed in a very simple manner and for a short period of time.

Further, the range in which foam is applied may be the whole head hair or may be only a specific portion.

Next, the applied foam is subjected to re-foaming on the head hair. The re-foaming may be performed by injecting gas, using an instrument such as a shaker and a brush, or using fingers, and it is more preferred to use fingers because the two-part hair dye composition may spread sufficiently to the roots of the head hair as well. The speed of foaming by using a shaker, a brush, or fingers is preferably controlled so as to prevent the foam from being spattered.

Here, re-foaming may be performed after the foam has disappeared completely, in the middle of foam disappearance, or before the applied foam is changed. Alternatively, re-foaming may be performed after the completion of the application to all the ranges in each of which foam is to be applied, or in the middle of the application. Re-foaming may be performed once continuously or may be performed multiple times intermittently. Here, if a shaker and a brush or fingers used for re-foaming are in contact with a part of the head hair continuously, or if they are departed away from a part of the head hair temporarily but come in contact with the part again within 1 second, the re-foaming is continuous. In short, a site to which foam is applied is observed, and foaming may be appropriately performed at least before a liquid drips from the applied foam. Liquid dripping may be prevented irrespective of the properties of foam by foaming disappearing foam again. In addition, even if foam has different properties based on the structure of the foamer container and the composition of the two-part hair dye composition, it is possible to change a foam quality to suitable one for hair dyeing by re-foaming. The foamer container having a specific structure and the two-part hair dye composition having a specific composition may prevent liquid dripping to provide the maintenance of a foam quality suitable for hair dyeing without re-foaming. However, even in such case, it is preferred that re-foaming be performed at least once by the timing as early as possible after the completion of the application of foam. Re-foaming may performed at the earlier timing to prevent color unevenness in the range to which foam should be applied. The timing is preferably within 5 minutes, more preferably within 3 minutes, and even more preferably within 1 minute after the completion of the application of the discharged foam to the head hair.

Hereinafter, a specific example of a preferred procedure in the steps of from discharging foam, applying the foam to the head hair, and re-foaming is exemplified with regard to partial hair dyeing and whole hair dyeing.

[Partial Hair Dyeing]

1) An appropriate amount of foam is discharged in one hand, the foam is applied to a part of the head hair, and one time of re-foaming is performed for 1 second to 10 minutes, and preferably 3 seconds to 3 minutes.

2) An appropriate amount of foam is discharged in one hand, the foam is applied to a part of the head hair, and 2 to 30 times of re-foaming are performed for 1 second to 10 minutes, and preferably 3 seconds to 3 minutes per one time. The re-foaming is performed for 2 seconds to 20 minutes, and preferably 5 seconds to 5 minutes in total.

[Whole Hair Dyeing]

3) An appropriate amount of foam is discharged in one hand, the foam is applied to a part of the head hair, and one time of re-foaming is performed for 3 seconds to 10 minutes, and preferably 5 seconds to 3 minutes. The foam is applied to the whole hair by repeating the operation.

4) An appropriate amount of foam is discharged in one hand, the foam is applied to a part of the head hair, and one time of re-foaming is performed for 3 seconds to 10 minutes, and preferably 5 seconds to 3 minutes. After the foam had been applied to the whole hair by repeating the operation, one time of re-foaming is performed for 3 seconds to 10 minutes, and preferably 5 seconds to 3 minutes. In addition, an appropriate amount of foam is discharged in one hand, the foam is additionally applied to a part of the head hair, and one time of re-foaming is performed over the whole hair for 3 seconds to 10 minutes, and preferably 5 seconds to 3 minutes.

5) An appropriate amount of foam is discharged in one hand, the foam is applied to a part of the head hair, and one time of re-foaming is performed for 3 seconds to 10 minutes, and preferably 5 seconds to 3 minutes. The foam is applied to the whole hair by repeating the operation. After the completion of the application to the whole hair, one time of re-foaming is performed for 3 seconds to 10 minutes, and preferably 5 seconds to 5 minutes.

6) An appropriate amount of foam is discharged in one hand, the foam is applied to a part of the head hair, and one time of re-foaming is performed for 3 seconds to 10 minutes, and preferably 5 seconds to 3 minutes. The foam is applied to the whole hair by repeating the operation. After the completion of the application to the whole hair, 2 to 30 times of re-foaming are performed over the whole hair for 3 seconds to 10 minutes, and preferably 5 seconds to 3 minutes per one time. The re-foaming is performed for 6 seconds to 20 minutes, and preferably 10 seconds to 5 minutes in total.

7) An appropriate amount of foam is discharged to a brush, and the foam is applied to a part of the head hair. The foam is applied to the whole hair by repeating the operation, and re-foaming is performed over the whole hair by using the same brush for 3 seconds to 10 minutes, and preferably 5 seconds to 5 minutes.

8) An appropriate amount of foam is discharged to a brush, the foam is applied to a part of the head hair, and one time of re-foaming is performed by using the same brush or hand for 3 seconds to 10 minutes, and preferably 5 seconds to 3 minutes. The foam is applied to the whole hair by repeating the operation. After the completion of the application to the whole hair, one time of re-foaming is performed by using the same brush or hand for 3 seconds to 10 minutes, and preferably 5 seconds to 5 minutes.

The range in which re-foaming is performed may be the whole head hair or may be only a specific portion. Even if application of foam is missed at a portion that is hardly confirmed such as hair in an occipital region of the head, the foam may be spread throughout by subjecting the whole head hair to re-foaming, which may prevent undyed hair from remaining. When only a specific portion is subjected to re-foaming in partial hair dyeing, the dyed border may be shaded off, leading to a natural finish. Further, when the re-foaming is performed, a portion throughout which the foam has spread can be visually confirmed very easily, which may prevent an undyed portion that should be dyed from remaining.

The foam is washed away after a lapse of time for about 3 to 60 minutes, and preferably about 5 to 45 minutes after the completion of the application of the foam. In the present invention, the time after the completion of the application of foam refers to the total time required from completely applying foam to the whole hair or a desired portion to rinsing the foam away, and is a concept that includes not only a time for simply allowing left to stand, but also a time required for re-foaming. After that, the hair is properly shampooed and rinsed, and then washed with water and dried.

EXAMPLES

Examples 1 to 10 and Comparative Examples 1 to 4

A first part and a second part having blend compositions (% by mass) as shown in Tables 1 to 3 were prepared. As illustrated in FIG. 1, 40 g of a first part (A1) was charged into a first container (2), and 60 g of a second part (A2) was charged into a second container (3) (also serving as container body (4) of squeeze container; internal volume: 210 mL), respectively. Further, a squeeze foamer (5) (S1 squeeze foamer manufactured by Daiwa Can Company) was prepared.

The charged first part and second part, and the squeeze foamer were given to specialized panelists (Japanese women aged in their 20's with shoulder-length black hair) and hair dyeing was performed in accordance with the following procedure.

"Hair Dyeing Procedure"

Figure 2:
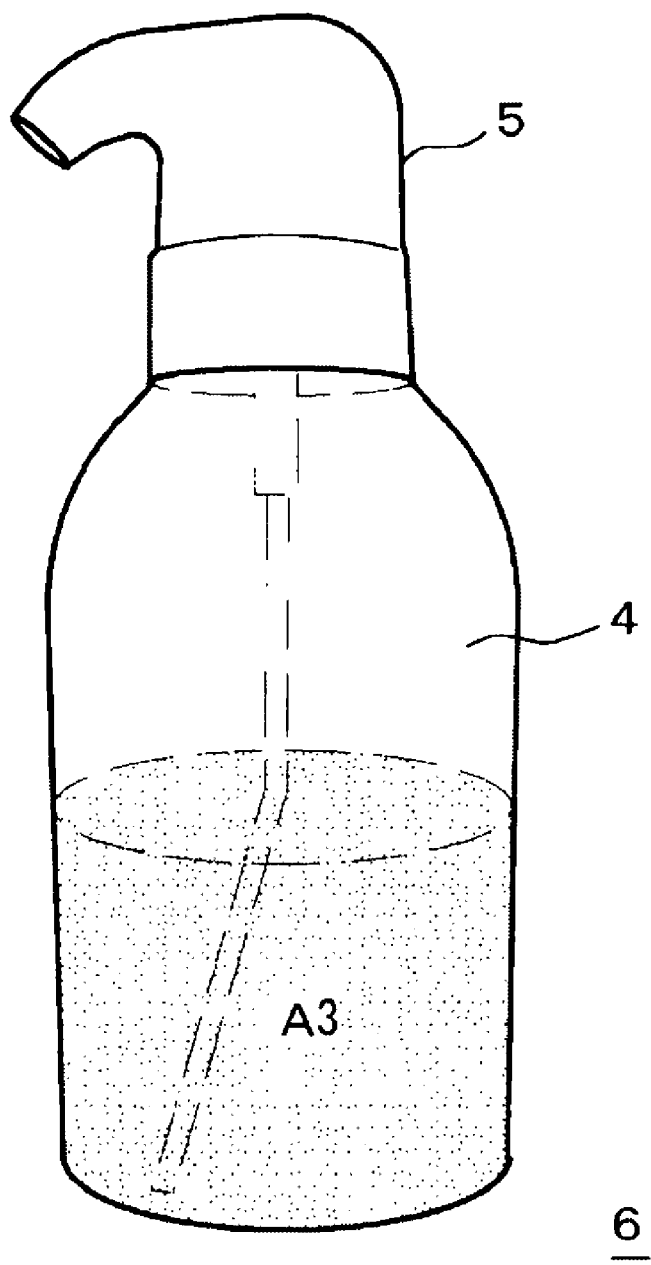
FIG. 2 is a drawing illustrating a two-part hair dye composition after mixing used in Examples and Comparative Examples.

1. 40 g of a first part are charged into a container body (4) of a squeeze container charged with 60 g of a second part, the first part and the second part are mixed with each other so as not to foam a liquid mixture, and then a squeeze foamer (5) is attached to the container body (FIG. 2).

2. After wearing of a glove, a squeeze container is squeezed by one hand under a state in which the squeeze container is upright, and a foamed liquid mixture is discharged in the palm of the other hand.

3. The foamed liquid mixture is applied to the dried head hair.

4. By repeating the operations according to the items 2 and 3, 80 g of the liquid mixture are applied to the whole head hair and the like.

5. The applied liquid mixture is re-foamed while the whole head hair is massaged with fingers for 15 seconds.

6. The hair is left to stand for 10 minutes.

7. The applied liquid mixture is re-foamed while the whole head hair is massaged with fingers for 25 seconds.

8. After the completion of the re-foaming operation according to the item 7, the hair is left to stand for 20 minutes.

9. The whole head hair is washed away with hot water, and shampooed, rinsed, and dried in the stated order.

With regard to "foaming property", "application property", "foam-holding property", and "conditioning effect", evaluations were performed in accordance with the following criteria, and the results were shown in the lower columns of blend compositions of Tables 1 to 3.

Foaming Property
A: An extremely uniform fine foam.
B: A uniform fine foam.
C: A nonuniform coarse foam.
D: No foam is formed, and water is mixed.

Application property (easiness of application and affinity to hair)
A: An agent is firmly fixed to the roots merely by pressing a foam on the head hair.
B: An agent can be easily fixed to the roots by running fingers through the hair.
C: An agent may not be fixed to some portions such as the roots in an occipital region of the head where the amount of the hair is large.
D: An agent shows a poor affinity, and undyed hair remains in the roots and the like.

Foam-Holding Property
A: A foam shows an extremely long duration and remains until being left to stand.
B: A foam has a sufficient duration and remains for a while after application.
C: A foam has such a duration that a problem does not occur in application, but disappears immediately after application.
D: A foam disappears immediately after discharge, and may cause liquid dripping during application.

Uneven Dyeing
A: No uneven dyeing is observed, and extremely uniform dyeing is provided.
B: Almost no uneven dyeing is observed, and uniform dyeing is provided.
C: A small degree of uneven dyeing is observed.
D: A large degree of uneven dyeing is observed.

Conditioning Effect
A: The hair after hair dyeing provides no coarse feeling, resulting in an extremely smooth finish.
B: The hair after hair dyeing provides almost no coarse feeling, resulting in a smooth finish.
C: The hair after hair dyeing provides a small degree of coarse and rough feeling.
D: The hair after hair dyeing provides a large degree of coarse and rough feeling.

TABLE 1

| (% by mass) | Example 1 | Example 2 | Comparative Example 1 | Comparative Example 2 | Comparative Example 3 | Comparative Example 4 |
|---|---|---|---|---|---|---|
| First part | | | | | | |
| p-Aminophenol | 0.1 | 0.1 | 0.1 | 0.1 | 0.1 | 0.1 |
| p-Amino-o-cresol | 0.1 | 0.1 | 0.1 | 0.1 | 0.1 | 0.1 |
| Toluene-2,5-diamine | 0.25 | 0.25 | 0.25 | 0.25 | 0.25 | 0.25 |
| Resorcin | 0.25 | 0.25 | 0.25 | 0.25 | 0.25 | 0.25 |
| Aqueous ammonia (28% by mass) | 8.5 | 8.5 | 8.5 | 8.5 | 8.5 | 8.5 |
| Ammonium hydrogen carbonate | 8.0 | 8.0 | 8.0 | 8.0 | 8.0 | 8.0 |
| Decyl glucoside | 3.2 | 3.2 | 3.2 | 3.2 | 3.2 | 3.2 |
| Laureth-23 | 2.0 | 2.0 | 2.0 | 2.0 | 2.0 | 2.0 |
| Propylene glycol | 4.0 | 4.0 | 4.0 | 4.0 | 4.0 | 4.0 |
| Polyquaternium-7 | 0.5 | — | — | 0.5 | — | — |
| Polyquaternium-39 | — | 0.5 | — | — | 0.5 | — |
| Polyquaternium-22 | — | — | 0.5 | — | — | 0.5 |
| EDTA-4Na | 0.1 | 0.1 | 0.1 | 0.1 | 0.1 | 0.1 |
| Ascorbic acid | 0.4 | 0.4 | 0.4 | 0.4 | 0.4 | 0.4 |
| Anhydrous sodium sulfite | 0.5 | 0.5 | 0.5 | 0.5 | 0.5 | 0.5 |
| Fragrance | 0.5 | 0.5 | 0.5 | 0.5 | 0.5 | 0.5 |
| Water | Balance | Balance | Balance | Balance | Balance | Balance |
| Second part | | | | | | |
| Aqueous hydrogen peroxide (35% by mass) | 16.3 | 16.3 | 16.3 | 16.3 | 16.3 | 16.3 |
| Sodium laureth sulfate | 1.9 | 1.9 | 1.9 | 1.9 | 1.9 | 1.9 |
| Lauric acid | 0.04 | 0.04 | 0.04 | 0.04 | 0.04 | 0.04 |
| Cetanol | 0.6 | 0.6 | 1.5 | 1.5 | 1.5 | 0.6 |
| Etidronic acid | 0.08 | 0.08 | 0.08 | 0.08 | 0.08 | 0.08 |
| Sodium hydroxide | * | * | * | * | * | * |
| Water | Balance | Balance | Balance | Balance | Balance | Balance |
| Viscosity of liquid mixture (first part:second part = 1:1.5) (5° C., mPa·s) | 5 | 5 | 40 | 33 | 35 | 7 |
| Evaluation — Foaming property | B | B | D | D | D | C |
| Evaluation — Application property | B | B | C | C | C | C |
| Evaluation — Foam-holding property | B | B | D | D | D | C |
| Evaluation — Uneven dyeing | A | A | C | C | C | C |
| Evaluation — Conditioning effect | B | B | C | C | C | C |

*: Amount for adjusting second part to pH 3.8

TABLE 2

| (% by mass) | Example 3 | Example 4 | Example 5 | Example 6 | Example 7 |
|---|---|---|---|---|---|
| First part | | | | | |
| m-Aminophenol | 0.15 | 0.15 | 0.15 | 0.15 | 0.15 |
| Toluene-2,5-diamine | 0.18 | 0.18 | 0.18 | 0.18 | 0.18 |
| Aqueous ammonia (28% by mass) | 6.0 | 6.0 | 6.0 | 6.0 | 6.0 |
| Ammonium hydrogen carbonate | 10.0 | 10.0 | 10.0 | 10.0 | 10.0 |
| Decyl glucoside | 6.0 | 6.0 | 6.0 | 6.0 | 6.0 |
| Laureth-23 | 2.0 | 2.0 | 2.0 | 2.0 | 2.0 |
| Propylene glycol | 4.0 | 4.0 | 4.0 | 4.0 | 4.0 |
| Ethanol | 7.0 | 7.0 | 7.0 | 7.0 | 7.0 |
| Polyquaternium-7 | 0.5 | — | 0.5 | — | 0.5 |
| Polyquaternium-39 | — | 0.5 | — | 0.5 | — |
| Polyquaternium-22 | — | — | 0.4 | 0.4 | 0.4 |
| EDTA-4Na | 0.1 | 0.1 | 0.1 | 0.1 | 0.1 |
| Ascorbic acid | 0.3 | 0.3 | 0.3 | 0.3 | 0.3 |
| Anhydrous sodium sulfite | 0.4 | 0.4 | 0.4 | 0.4 | 0.4 |
| Fragrance | 0.5 | 0.5 | 0.5 | 0.5 | 0.5 |
| Water | Balance | Balance | Balance | Balance | Balance |
| Second part | | | | | |
| Aqueous hydrogen peroxide (35% by mass) | 16.3 | 16.3 | 16.3 | 16.3 | 16.3 |
| Sodium laureth sulfate | 0.5 | 0.5 | 0.5 | 0.5 | 0.7 |
| Octoxyglycerin | 0.1 | 0.1 | 0.1 | 0.1 | 0.1 |
| Lauramidopropyl betaine | 0.05 | 0.05 | 0.05 | 0.05 | 0.02 |
| Lauryl hydroxysultaine | 0.05 | 0.05 | 0.05 | 0.05 | 0.02 |
| Lauric acid | 0.01 | 0.01 | 0.01 | 0.04 | 0.04 |
| Cetanol | 0.58 | 0.58 | 0.58 | 0.58 | 0.58 |
| Stearyl alcohol | 0.15 | 0.15 | 0.15 | 0.2 | 0.2 |
| Oxyquinoline sulfate | 0.04 | 0.04 | 0.04 | 0.04 | 0.04 |
| Etidronic acid | 0.08 | 0.08 | 0.08 | 0.08 | 0.08 |
| Sodium hydroxide | * | * | * | * | * |
| Water | Balance | Balance | Balance | Balance | Balance |
| Viscosity of liquid mixture (first part:second part = 1:1.5) (5° C., mPa·s) | 2 | 2 | 2 | 3 | 3 |
| Evaluation Foaming property | A | A | A | A | A |
| Application property | A | A | A | A | A |
| Foam-holding property | A | A | A | A | A |
| Uneven dyeing | A | A | A | A | A |
| Conditioning effect | B | B | B | B | B |

*: Amount for adjusting second part to pH 3.8

TABLE 3

| (% by mass) | Example 8 | Example 9 | Example 10 |
|---|---|---|---|
| First part | | | |
| Toluene-2,5-diamine | 0.14 | 0.14 | 0.14 |
| p-Phenylenediamine | 0.1 | 0.1 | 0.1 |
| m-Aminophenol | 0.05 | 0.05 | 0.05 |
| p-Amino-o-cresol | 0.1 | 0.1 | 0.1 |
| 2,4-Diaminophenoxyethanol hydrochloride | 0.15 | 0.15 | 0.15 |
| Aqueous ammonia (28% by mass) | 6.0 | 6.0 | 6.0 |
| Ammonium hydrogen carbonate | 10.5 | 10.5 | 10.5 |
| Decyl glucoside | 6.5 | 6.5 | 6.5 |
| Trideceth-9 | 0.6 | 0.6 | 0.6 |
| Laureth-23 | 1.8 | 1.8 | 1.8 |
| Sodium laureth sulfate | 2.3 | 3.3 | 4.4 |
| Myristyl alcohol | 0.2 | 0.2 | 0.2 |
| Propylene glycol | 4.0 | 4.0 | 4.0 |
| Ethanol | 9.0 | 9.0 | 9.0 |
| Polyquaternium-7 | 0.6 | 0.6 | 0.6 |
| Polyquaternium-22 | 0.4 | 0.4 | 0.4 |
| EDTA-4Na | 0.1 | 0.1 | 0.1 |
| Ascorbic acid | 0.3 | 0.3 | 0.3 |
| Anhydrous sodium sulfite | 0.4 | 0.4 | 0.4 |
| Fragrance | 0.5 | 0.5 | 0.5 |
| Water | Balance | Balance | Balance |
| Second part (common) | | | |
| Aqueous hydrogen peroxide (35% by mass) | 16.3 | 16.3 | 16.3 |
| Sodium laureth sulfate | 0.4 | 0.4 | 0.4 |
| Octoxyglycerin | 0.05 | 0.05 | 0.05 |
| Lauramidopropyl betaine | 0.02 | 0.02 | 0.02 |
| Lauryl hydroxysultaine | 0.02 | 0.02 | 0.02 |
| Lauric acid | 0.01 | 0.01 | 0.01 |
| Cetanol | 0.35 | 0.35 | 0.35 |
| Stearyl alcohol | 0.15 | 0.15 | 0.15 |
| Oxyquinoline sulfate | 0.04 | 0.04 | 0.04 |
| Etidronic acid | 0.08 | 0.08 | 0.08 |
| Sodium hydroxide | * | * | * |
| Water | Balance | Balance | Balance |
| Viscosity of liquid mixture (first part:second part = 1:1.5) (5° C., mPa·s) | 20 | 20 | 24 |
| Evaluation Foaming property | A | A | B |
| Application property | A | A | A |
| Foam-holding property | A | A | A |
| Uneven dyeing | A | A | A |
| Conditioning effect | B | B | B |

* Amount for adjusting second part to pH 3.8

The invention claimed is:

1. A two-part hair dye composition, comprising a first part comprising an alkali agent, a second part comprising hydrogen peroxide, and a non-aerosol type foamer container for discharging a liquid mixture of the first part and the second part as a foam, wherein the liquid mixture comprises the following components (A) to (D):
   (A) 0.1 to 5% by mass of an alkyl sulfate or a polyoxyalkylene alkyl sulfate;
   (B) 0.1 to 10% by mass of an alkyl polyglucoside;
   (C) 0.01 to 3% by mass of a dimethyldiallyl ammonium chloride-acrylamide copolymer or a dimethyldiallyl ammonium chloride-acrylamide-acrylic acid copolymer; and
   (D) 0.01 to 0.8% by mass of a higher alcohol.

2. The two-part hair dye composition according to claim 1, wherein a mass ratio of the component (A) to the component (B) (a content of the component (A)/a content of the component (B)) in the liquid mixture of the first part and the second part is 0.05 to 0.8.

3. The two-part hair dye composition according to claim 1 or 2, wherein a mass ratio of the component (A) to the component (C) (a content of the component (A)/a content of the component (C)) in the liquid mixture of the first part and the second part is 0.1 to 10.

4. The two-part hair dye composition according to claim 1, further comprising 0.01 to 4% by mass of a nonvolatile hydrophilic solvent in the liquid mixture of the first part and the second part.

5. The two-part hair dye composition according to claim 1, wherein a content of a silicone in the liquid mixture of the first part and the second part is 0.5% by mass or less.

6. A head hair dyeing method, comprising discharging the liquid mixture of the two-part hair dye composition according to claim 1 as a foam from a non-aerosol type foamer container; applying the foam to a head hair; and then re-foaming on the head hair.

* * * * *